US009532585B2

(12) United States Patent
Rowe et al.

(10) Patent No.: US 9,532,585 B2
(45) Date of Patent: Jan. 3, 2017

(54) INGESTIBLE COMPOSITIONS CONTAINING AN ODORIFEROUS OIL

(75) Inventors: Dennis Rowe, Swindon (GB); Kelvin Royce Garnett, Swindon (GB)

(73) Assignee: R.P. Scherer Technologies, LLC, Carson City, NV (US)

( * ) Notice: Subject to any disclaimer, the term of this patent is extended or adjusted under 35 U.S.C. 154(b) by 818 days.

(21) Appl. No.: 10/466,896

(22) PCT Filed: Jan. 16, 2002

(86) PCT No.: PCT/GB02/00164
§ 371 (c)(1),
(2), (4) Date: Jan. 12, 2004

(87) PCT Pub. No.: WO02/056709
PCT Pub. Date: Jul. 25, 2002

(65) Prior Publication Data
US 2004/0121000 A1    Jun. 24, 2004

(51) Int. Cl.
*A61K 35/60*   (2006.01)
*A61K 36/752*  (2006.01)
*A61K 36/534*  (2006.01)
*A23D 9/007*   (2006.01)
*A61K 9/48*    (2006.01)

(52) U.S. Cl.
CPC .............. *A23D 9/007* (2013.01); *A23L 33/10* (2016.08); *A23L 33/115* (2016.08); *A23P 10/30* (2016.08); *A61K 9/4858* (2013.01)

(58) Field of Classification Search
CPC ...................................................... A61K 35/60
USPC ....................................................... 424/554
See application file for complete search history.

(56) References Cited

U.S. PATENT DOCUMENTS

| | | | | |
|---|---|---|---|---|
| 4,731,979 | A | * | 3/1988 | Yamamoto et al. ............. 53/529 |
| 4,853,247 | A | * | 8/1989 | Barcelon et al. ............. 426/613 |
| 4,913,921 | A | | 4/1990 | Schroeder et al. |
| 4,961,939 | A | | 10/1990 | Antrim et al. |
| 5,603,951 | A | * | 2/1997 | Woo .............................. 424/455 |
| 5,650,157 | A | * | 7/1997 | Bockow ................ A61K 8/925 424/401 |
| 5,853,761 | A | | 12/1998 | Kumabe et al. |
| 5,900,251 | A | | 5/1999 | Raissen |
| 6,056,971 | A | | 5/2000 | Goldman |
| 6,284,268 | B1 | * | 9/2001 | Mishra et al. ................ 424/455 |
| 6,346,231 | B1 | * | 2/2002 | Opheim ............... A61K 9/4816 424/45 |
| 6,641,837 | B2 | * | 11/2003 | Opheim ............... A61K 9/4816 424/451 |

FOREIGN PATENT DOCUMENTS

| | | |
|---|---|---|
| CA | 2293088 | 6/2000 |
| DE | 19854987 | 5/2000 |
| EP | 0127297 | 12/1984 |
| EP | 0276772 | 8/1988 |
| EP | 0296117 | 12/1988 |
| GB | 2324457 | 10/1998 |
| GB | 2349817 A * | 11/2000 |
| GB | 232349817 | 11/2000 |
| JP | S55-105623 A | 8/1980 |
| JP | S56-65820 A | 6/1981 |
| JP | S61-15647 | 1/1986 |
| JP | S61-15649 | 1/1986 |
| JP | 3-130042 | 6/1991 |
| JP | H04-507418 | 12/1992 |
| JP | 06-000068 | 1/1994 |
| JP | H06-133707 | 5/1994 |
| JP | H07-204487 | 8/1995 |
| JP | 09-084557 | 3/1997 |
| JP | H10-503750 | 4/1998 |
| JP | 10-251143 | 9/1998 |
| JP | 410 251143 A * | 9/1998 |
| JP | 2001-131575 | 5/2001 |
| WO | 89/02223 | 3/1989 |
| WO | 9102520 | 3/1991 |
| WO | 95/24893 | 9/1995 |
| WO | 98/42319 | 10/1998 |

OTHER PUBLICATIONS

Hard Capsules, K. Ridgeway, ed., Pharmaceutical Press, London, pp. 157-163, 199, 200, 203, 219, 220, 224, 225, 258, 267-269 and 286 (1987).
M.E. Stansby, "Flavors and Odors of Fish Oils", J. Am. Oil Chemist's Soc., vol. 48, No. 12, pp. 820-823 (1971).
J.P. Stanley, "Soft Gelain Capsules", The Theory and Practice of Industrial Pharmacy, Lea & Febiger, Philadelphia, L. Lachman et al., eds. pp. 404-420 (1976).

* cited by examiner

*Primary Examiner* — Chris R Tate
(74) *Attorney, Agent, or Firm* — Fitzpatrick, Cella, Harper & Scinto

(57) ABSTRACT

An ingestible composition contained in a soft gel or shard shell capsule includes a digestible odoriferous oil such as a fish oil which can cause reflux or eructation odor problems on the breath of a person taking the capsule. This is reduced by including in the ingestible composition at least one surfactant, preferably in an amount of about 2 to about 20% weight and at least one edible odor-masking ingredient such as parsley seed oil, lemon balm, lemon grass oil, fennel, peppermint oil and/or menthol.

16 Claims, No Drawings

US 9,532,585 B2

INGESTIBLE COMPOSITIONS CONTAINING AN ODORIFEROUS OIL

RELATED APPLICATIONS

This application is a filing under 35 U.S.C. §371 and is based upon International Application No. PCT/GB02/00164 filed Jan. 16, 2002 and claims priority to GB Application No. 0101980 filed Jan. 17, 2001.

TECHNICAL FIELD

This invention relates to ingestible compositions containing at least one digestible odoriferous oil such as fish oil, and is more particularly concerned with such ingestible compositions when formulated in a capsule such as a soft gel or hard shell capsule.

BACKGROUND ART

WO-A-95/24893 discloses a delivery system for a hydrophobic drug. Bioavailability of the hydrophobic drug is improved in vivo by the use of a drug carrier system comprising a digestible oil and a relatively high level of a pharmaceutically acceptable surfactant component including a hydrophilic surfactant component which inhibits in vivo lipolysis of the oil and a lipophilic surfactant component capable of substantially reducing the inhibitory effect of the hydrophilic surfactant component. The digestible oils disclosed are not those which have an odor which is generally regarded as being offensive. EP-A-0127297 discloses encapsulated vitamin or mineral compositions in which the bioavailability of, inter alia, oil-soluble vitamins is improved by including 30 to 80% (preferably 35 to 75%) by weight of a polyoxyethylene sorbitan ester such as Polysorbate 80 in the composition, with the objective of forming a microemulsion of the oil-soluble vitamins in the gastrointestinal tract. The composition may further include a diluent in the form of an alcohol, a vegetable oil or a derivative thereof. Thus, EP-A-0127927 is not concerned with mitigating the problems of eructation following ingestion of an odoriferous oil such as fish oil.

WO 98/42319 discloses essentially non-aqueous compositions for oral administration which contain a biologically active oil or oil-soluble ingredient, such as oil-soluble vitamins, maintained as a dispersion in a carrier oil by means of an emulsifier system having an HLB (hydrophobic/lipophilic balance) value of 10 to 18. The objective of this is similar to that of EP-A-0127297, namely to improve bioavailability of the active ingredient by causing it to become finely dispersed in the gastric juices upon administration. The use of fish oils amongst a large number of possible biologically active oil or oil-soluble ingredient is disclosed, but there is no mention of the eructation problems associated with the use of such oils. The avoidance of undesirable taste is mentioned as an advantage of using a capsule dosage form as compared with a liquid dosage form.

U.S. Pat. No. 6,056,971 discloses a method of enhancing the dissolution properties in the gastrointestinal tract of relatively water-insoluble dietary supplements, particularly coenzyme Q-10 (ubiquinone). The method involves mixing a non-ionic surfactant with a polyhydric alcohol to form a uniform mixture and then mixing in the dietary supplement to form a non-aqueous solution which contains about 20 to 90% by weight of the surfactant and about 2 to 50% by weight of the polyhydric alcohol. The solution can then be encapsulated in a soft gel capsule. There is no mention of the eructation problems associated with the ingestion of odoriferous oils such as fish oil.

U.S. Pat. No. 5,900,251 discloses an essentially herbal or herbal extract composition for the treatment and control of breath odors and for aiding digestion, which contains ginger, licorice, chamomile, parsley seed oil and sunflower seed oil in an ingestible delivery system such as a capsule. The ginger, the licorice and the chamomile are present as preferred herbal or herbal extract digestive aids and none of those has an odor which is generally regarded as being offensive. The parsley seed oil is present as a preferred breath cleansing ingredient for cleansing the breath of odors, such as that of chime, generated in the stomach and/or other portions of the intestinal tract. The sunflower seed oil is present as a preferred ingestible oil carrier. The composition further includes an emulsifier and a suspending agent. The suspending agent is provided to suspend the active ingredients in the oil carrier. The emulsifier is typically selected from natural emulsifiers, synthetic surface active agents and solid particle emulsifiers. The purpose of including the emulsifier is not specifically disclosed, although it may be deduced from column 2, lines 54 to 58, that it is present to provide, together with the oil carrier and the suspending agent, a suitable delivery vehicle so that the active ingredients can be delivered to the stomach or lower in the digestible tract without significant release in the oral cavity, throat or esophagus.

GB 2324457 discloses a dietary supplement comprising a nutritional oil emulsified into water with an emulsifying agent to form a micellised droplet. This droplet is encapsulated with a modified starch such as a vegetable oligosaccharide. The modified starch coating serves to protect the oil from degradation by exposure to oxygen and UV light. The starch coating also masks the flavor, odor and texture of the oil.

WO 89/02223 is concerned with preventing flavor degradation of non-hydrogenated fish oils in stable emulsions such as salad dressings. The improvement is obtained by the incorporation into the food product of small amounts of fructose. An oil soluble flavor masking agent such as lemon oil may also be included in the product. Similarly, U.S. Pat. No. 4,961,939 is concerned with the prevention of formation of malodorous alcohols and aldehydes from water-in-oil or oil-in-water emulsions containing fish oil, whereby to eliminate undesired odor and off-taste.

GB 2349817 discloses a soft gelatin capsule having a masking agent added to the capsule contents and a masking agent incorporated into the capsule shell itself. Orange oil is given as an example of the masking agent. The product is said to have improved taste during swallowing, reduced rebound aftertaste and reduced odor.

CA 2293088 is concerned with masking the odor and taste of fish oil in, for example, dietary supplements, without introducing a stronger taste or scent. This is achieved by mixing the fish oil to be masked with thyme essence. It is a particular problem with ingestible compositions containing such odoriferous oils as fish oils that eructation (or reflux) tends to occur soon after ingestion, resulting in an unpleasant taste in the mouth and a very unpleasant odor on the breath of the person ingesting such a composition, even when the composition has been swallowed whole without chewing.

DISCLOSURE OF THE INVENTION

It is an object of the present invention to provide an improved ingestible composition for delivering a digestible but unpleasantly odoriferous oil and having reduced post-ingestion odor.

The invention provides for a capsule for delivering an odoriferous oil and having reduced post-ingestion odor, said capsule containing a substantially non-aqueous ingestible composition comprising at least one digestible odoriferous oil, at least one edible odor-masking ingredient, and at least one edible surfactant.

The invention further provides for the use of a combination of at least one edible odor-masking ingredient and at least one edible surfactant in a substantially non-aqueous ingestible composition containing at least one digestible odoriferous oil, for reducing the post-ingestion odor of said at least one digestible odoriferous oil.

The invention also provides a method of reducing the post-ingestion odor of a substantially non-aqueous oral ingestible composition containing at least one odoriferous oil, comprising including in an oral ingestible composition at least one edible odor-masking ingredient and at least one edible surfactant.

The ingestible composition is preferably a continuous phase, substantially non-aqueous system. The composition may be in the form of an emulsion concentrate or paste.

Said at least one edible surfactant is present in an amount effective, upon ingestion, to bind said at least one digestible odoriferous oil in an emulsion in the stomach. Preferably, said at least one edible surfactant is present in the range of about 2 to about 20% by weight of the total weight of the ingestible composition, and preferably towards the lower end of this range, for example about 2 to about 10%, about 2 to about 7% or about 5 to about 7%, by weight. By using relatively low levels of said at least one edible surfactant, it has been found that, upon ingestion, a relatively coarse emulsion of the digestible odoriferous oil is formed in the stomach which, in combination with said at least one odor-masking ingredient substantially reduces the taste and odor problem after eructation. The coarse emulsion formed in the stomach binds said at least one digestible odoriferous oil in the form of coarse droplets which have the surfactant at the surfaces thereof, thereby reducing the amount of odiferous oil capable of being released. Said at least one edible odor-masking ingredient is also bound but has fragments capable of remaining in the aqueous portion of the stomach so being more effective.

The emulsification of a digestible odoriferous oil to produce a bi-phasic mixture using fats and water and a very small amount of surfactant (about 0.4% of the total composition) in the actual ingestible composition for use in capsules has been previously proposed. With such a composition, only a relatively slow breakdown on the matrix of the fats and oil occurs in the stomach, thereby resulting in the odor being released only slowly. However, it also means that the oil is only slowly available for digestion.

The presence of said at least one edible surfactant in the ingestible composition according to the present invention allows the digestible odoriferous oil to be dispersed immediately, or upon dissolution of the capsule in the case where the ingestible composition is contained in a capsule.

Said at least one edible surfactant may be selected from the group consisting of hydrophilic surfactants, lipophilic surfactants and mixtures thereof. Said at least one edible surfactant is preferably a mixture of at least one hydrophilic surfactant and at least one lipophilic surfactant.

The weight ratio of said at least one hydrophilic surfactant to said at least one lipophilic surfactant is generally in the range of about 1:1.5 to about 1:2.5, usually about 1:1.7 to about 1:2.1.

Suitable hydrophilic surfactants include, but are not limited to, polyoxyethylene glycerides of $C_{10}$ to $C_{18}$ fatty acids.

Said at least one hydrophilic surfactant is preferably selected from the group consisting of polyoxyethylene sorbitan mono-oleates, polyoxyethylene hydrogenated castor oils, and combinations thereof. More specifically, said at least one hydrophilic surfactant may be selected from the group consisting of polyoxyethylene sorbitan mono-oleate sold under the Registered Trade Mark POLYSORBATE 80 BPC, polyoxyethylene (40) hydrogenated castor oil (such as that commercially available under the Registered Trade Mark CREMOPHOR RH40), and combinations thereof.

Suitable lipophilic surfactants include, but are not limited to, glycerides of $C_5$ to $C_{10}$ fatty acids. For example, said at least one lipophilic surfactant may be selected from the group consisting of sorbitan mono-oleate, glyceryl mono-caprylate, glyceryl di-caprylate, glyceryl mono-caprate, glyceryl di-caprate, and combinations of any two or more of these. More specifically, said at least one lipophilic surfactant may be selected from the product commercially available under the Registered Trade Mark IMWITOR 988, the product commercially available under the Registered Trade Mark IMWITOR 742, the product commercially available under the Registered Trade Mark CAPMUL MCM, and combinations of any two or more of these.

Said at least one digestible odoriferous oil may be selected from the group consisting of fish oils, odoriferous vegetable oils, other digestible oils having an unpleasant odor on the breath of a person ingesting the composition, and combinations of any two or more of these oils. Examples of these oils include cod liver oil, shark liver oil, halibut liver oil, fish oil from more than one species and fish oil concentrates (such as those supplied under the Registered Trade Mark EPAX).

The amount of said at least one digestible odoriferous oil may be from about 75 to about 98%, preferably from about 85 to about 98%, by weight based on the total weight of the composition. However, said amount of said at least one digestible odoriferous oil may be much lower (e.g., as low as 30%) In, for example, compositions of multivitamins or other supplements which contain relatively high levels of inorganic salts and/or other non-oily materials. Suitable edible odor-masking ingredients include, but are not limited to, odor-masking oils. For examples, said at least one odor-masking ingredient may be selected from the group selected from parsley seed oil, lemon balm, lemon grass oil, fennel, peppermint oil, menthol and combinations of any two or more of these.

Said at least one edible odor-masking ingredient is present in an amount effective to at least partially mask the odor of said at least one digestible odoriferous oil. Depending upon the nature of the odor-masking ingredient used and the nature of the odoriferous oil(s), the odor-masking ingredient(s) may be present in an amount of about 0.01 to about 5 wt. % based on the total weight of said at least one digestible odoriferous oil.

The ingestible composition of the present invention may readily be prepared by simply mixing the ingredients together at room temperature. However, when the surfactant is a mixture of lipophilic and hydrophilic surfactants, the lipophilic surfactant(s) will normally be added first and the mixture homogenised before addition of the hydrophilic surfactant(s).

The ingestible composition may be encapsulated in soft gel or hard shell capsules. Methods of soft gel encapsulation are disclosed in "Theory & Practice of Industrial Pharmacy" by Lachman & Leibermann, $2^{nd}$ edition, published by Henry Kimpton Publishers, London. Methods of liquid-fill hard-shell encapsulation are disclosed in "Hard capsules—Development and Technology" edited by K. Ridgeway, published by Pharmaceutical Press 1987, the disclosure of which are incorporated herein by reference. The present invention will now be described, in future detail, in the following Examples:—

EXAMPLE 1

An ingestible composition was formulated by mixing together the following ingredients in the following weight proportions:

| | |
|---|---|
| 1.22 | Parsley seed oil (odor masking ingredient) |
| 25.0 | Sorbitan mono-oleate BP (lipophilic surfactant) |
| 12.2 | ® POLYSORBATE 80 BP (hydrophilic surfactant) |
| 0.02 | Cholecalciferol C (oily) BP/EP (Vitamin D) |
| 0.26 | DL Alpha Tocopheryl Acetate USP (Vitamin E) |
| 1.02 | Synthetic Vitamin A concentrate BP/EP, 1 M iu/g |
| 480 | Cod liver oil (® OCEAN GOLD CLO PC0224) |

Using standard soft gel capsule manufacturing technology, the above composition was filled into gelatin capsules formed from a gelatin base comprising the following ingredients:—

| | |
|---|---|
| 200 | Glycerin BP/EP/USP |
| 366 | Purified water BP/EP/USP |
| 434 | Gelatin, 150 Bloom EP |

Each capsule contained 520 mg of the ingestible composition.

EXAMPLE 2

Example 1 was repeated to produce capsules each containing 1040 mg of the ingestible composition.

The following tests were conducted using the capsules of Examples 1 and 2:—

1. A capsule of Example 2 (1040 mg size chosen as likely to give biggest effect) was swallowed by a subject who reported that no eructation occurred within 2 hours of ingestion. In contrast, the same subject reported that a capsule without the surfactant and parsley system resulted in eructation within 10-15 minutes.
2. A capsule of Example 1 was chewed by a subject so that it ruptured in the mouth. A slight initial fishy taste was reported before the parsley seed oil was sensed, but this was the only fish-type taste noted. Even 5 minutes afterwards, the subject reported that no residual fish taste was noticeable. In contrast, if a conventional capsule containing fish oil without any surfactant or odor-masking ingredient is chewed to cause it to rupture in the mouth, the taste is so immediately repellent that some subjects retch and most report that the taste remains for 10 minutes or more.
3. The contents of a capsule of Example 2 were squeezed into a vial containing approximately 15 ml tap water and capped. A single inversion formed a coarse emulsion but on smelling the vial contents, no fish odor could be detected, only the odor-masking material, parsley seed oil. The emulsion droplets did coalesce with time but did not form a completely separated layer as does an oil-filled capsule. Even after several hours there was still no odor present from the vial.

EXAMPLE 3

Multivitamin Formulation

An ingestible composition was formulated by mixing together the ingredients tabulated below. The weight proportions and percentages are also given. Unless indicated otherwise the individual components were of the same source and/or grade as those listed for Example 1 above.

| Material | mg/capsule | % |
|---|---|---|
| Calcium Carbonate BP/EP | 508.000 | 40.54 |
| Borage Oil | 26.830 | 2.14 |
| Ferrous Fumarate | 21.980 | 1.75 |
| Zinc Sulphate | 20.700 | 1.65 |
| Lecithin | 16.507 | 1.32 |
| DL Alpha Tocopheryl Acetate | 7.599 | 0.61 |
| Fat Mix | 103.582 | 8.27 |
| Glucosamine Sulphate (K salt) | 67.500 | 5.39 |
| Chondriotin Sulphate | 55.550 | 4.43 |
| Pulse Oil (Seven Seas Ltd.) | 100.063 | 7.99 |
| Devitaminised Cod Liver Oil (Seven Seas Ltd.) | 285.633 | 22.80 |
| Parsley Seed Oil | 1.000 | 0.08 |
| Sorbitan Mono Oleate BP | 18.000 | 1.44 |
| POLYSORBATE 80 BP (hydrophilic surfactant) | 9.000 | 0.72 |
| Beta carotene 30% Suspension | 6.974 | 0.56 |
| Korean Ginseng Extract 5:1 | 2.000 | 0.16 |
| Ginger Extract 3:1 | 2.000 | 0.16 |
| Sodium Selenite Pentahydrate | 0.0832 | Trace |
| Total | 1253.0012 | |

Using standard soft gel capsule manufacturing technology, the above composition was filled into non-gelatin capsules and formed for the following ingredients in the indicated relative proportions:

| | |
|---|---|
| 182.6 | Glycerin BP/EP/USP |
| 500.0 | Purified Water BP/EP/USP |
| 234.6 | Modified Starch |
| 75.9 | carrageenan |
| 6.9 | Sodium Diphosphate |
| 1.04 | Red Iron Oxide paste E172 |
| 4.96 | Black Iron Oxide paste E172 |

A test subject reported only two small eructations, one at 15 minutes after ingestion of a single capsule and a second after approximately 20 minutes.

EXAMPLES of 4 to 13

Ingestible compositions were formed by mixing together the ingredients as tabulated below. The compositions were not formed into capsules. Testing was carried out by a test subject ingesting a weighed amount of composition (given as mg/capsule equivalent) in the as-mixed form (i.e., oil or paste).

EXAMPLE 4

| Material | mg/capsule equivalent | % |
|---|---|---|
| Calcium Carbonate BP/EP | 508.000 | 40.97 |
| Borage Oil | 26.832 | 2.16 |
| Ferrous Fumarate | 21.980 | 1.77 |

| Material | mg/capsule equivalent | % |
|---|---|---|
| Zinc Sulphate | 20.700 | 1.67 |
| Lecithin | 16.508 | 1.33 |
| Vitamin E | 7.600 | 0.61 |
| Fat Mix | 103.584 | 8.35 |
| Glucosamine Sulphate (K salt) | 67.500 | 5.44 |
| Chondriotin Sulphate | 55.552 | 4.48 |
| Pulse Oil (Seven Seas Ltd.) | 100.064 | 8.07 |
| Devitaminized Cod Liver Oil (Seven Seas Ltd.) | 285.632 | 23.04 |
| Parsley Seed Oil | 1.000 | 0.081 |
| Sorbitan Mono Oleate BP | 12.520 | 1.00 |
| POLYSORBATE 80 BP (hydrophilic surfactant) | 12.520 | 1.00 |
| Total | 1239.968 | |

The mixture produced was a paste. The test subject reported that fish oil was discernible and the composition had an unpleasant taste.

EXAMPLE 5

| Material | mg/capsule equivalent | % |
|---|---|---|
| Calcium Carbonate BP/EP | 508.000 | 40.97 |
| Borage Oil | 26.832 | 2.16 |
| Ferrous Fumarate | 21.980 | 1.77 |
| Zinc Sulphate | 20.700 | 1.67 |
| Lecithin | 16.508 | 1.33 |
| Vitamin E | 7.600 | 0.61 |
| Fat Mix | 103.584 | 8.35 |
| Glucosamine Sulphate (K salt) | 67.500 | 5.44 |
| Chondriotin Sulphate | 55.552 | 4.48 |
| Pulse Oil (Seven Seas Ltd.) | 100.064 | 8.07 |
| Devitaminized Cod Liver Oil (Seven Seas Ltd.) | 285.632 | 23.04 |
| Parsley Seed Oil | 1.000 | 0.081 |
| POLYSORBATE 80 BP (hydrophilic surfactant) | 25.040 | 2.0 |
| Total | 1239.968 | |

The mixture produced was a paste. As with Example 4, the test subject reported that fish oil was discernible and the composition had an unpleasant taste.

EXAMPLE 6

| Material | mg/capsule equivalent | % |
|---|---|---|
| Calcium Carbonate BP/EP | 508.000 | 39.70 |
| Borage Oil | 26.832 | 2.10 |
| Ferrous Fumarate | 21.980 | 1.72 |
| Zinc Sulphate | 20.700 | 1.62 |
| Lecithin | 16.508 | 1.29 |
| Vitamin E | 7.600 | 0.59 |
| Fat Mix | 103.584 | 8.10 |
| Glucosamine Sulphate (K salt) | 67.500 | 5.28 |
| Chondriotin Sulphate | 55.552 | 4.34 |
| Pulse Oil (Seven Seas Ltd.) | 100.064 | 7.82 |
| Devitaminized Cod Liver Oil (Seven Seas Ltd.) | 285.632 | 22.32 |
| Parsley Seed Oil | 1.000 | 0.078 |
| POLYSORBATE 80 BP (hydrophilic surfactant) | 64.52 | 5.04 |
| Total | 1279.448 | |

The mixture produced was a paste. The test subject reported that fish oil was barely discernible and over-ridden by a stronger parsley seed oil taste.

EXAMPLE 7

| Material | mg/capsule equivalent | % |
|---|---|---|
| Calcium Carbonate BP/EP | 508.000 | 37.60 |
| Borage Oil | 26.832 | 1.99 |
| Ferrous Fumarate | 21.980 | 1.63 |
| Zinc Sulphate | 20.700 | 1.53 |
| Lecithin | 16.508 | 1.22 |
| Vitamin E | 7.600 | 0.56 |
| Fat Mix | 103.584 | 7.67 |
| Glucosamine Sulphate (K salt) | 67.500 | 5.00 |
| Chondriotin Sulphate | 55.552 | 4.11 |
| Pulse Oil (Seven Seas Ltd.) | 100.064 | 7.41 |
| Devitaminized Cod Liver Oil (Seven Seas Ltd.) | 285.632 | 21.14 |
| Parsley Seed Oil | 1.000 | 0.074 |
| POLYSORBATE 80 BP (hydrophilic surfactant) | 136.24 | 10.08 |
| Total | 1351.168 | |

The mixture produced was a paste. The test subject reported that no fish oil was discernible, but the parsley seed oil taste was stronger than that reported for Example 6.

EXAMPLE 8

| Material | mg/capsule equivalent | % |
|---|---|---|
| Fish Oil 18/12 (EPAX 3000TG, Pronova) | 480 | 94.78 |
| Sorbitan Mono-oleate BP | 16.81 | 3.32 |
| POLYSORBATE 80 BP (hydrophilic surfactant) | 8.42 | 1.66 |
| Parsley Seed Oil | 1.22 | 0.25 |
| Total | 506.45 | |

The mixture produced was a single continuous non-aqueous phase. The test subject reported that the fish oil was at the point of detection in the mouth.

EXAMPLE 9

| Material | mg/capsule equivalent | % |
|---|---|---|
| Fish Oil 18/12 (EPAX 3000TG, Pronova) | 480 | 96.76 |
| Sorbitan Mono-oleate BP | 9.9 | 2.00 |

-continued

| Material | mg/capsule equivalent | % |
| --- | --- | --- |
| POLYSORBATE 80 BP (hydrophilic surfactant) | 4.95 | 1.00 |
| Parsley Seed Oil | 1.22 | 0.25 |
| Total | 496.07 | |

The mixture produced was a single continuous non-aqueous phase. The test subject reported that fish oil was discernible in the mouth.

EXAMPLES 10 AND 11

| Material | mg/capsule equivalent | % (Ex. 6) | % (Ex. 7) |
| --- | --- | --- | --- |
| Calcium Carbonate BP/EP | 677.12 | 52.72 | 52.68 |
| Cod Liver Oil | 500 | 38.93 | 38.89 |
| Sorbitan Mono-oleate BP | 17.12 | 1.33 | 1.33 |
| POLYSORBATE 80 BP (hydrophilic surfactant) | 8.56 | 0.66 | 0.66 |
| Peppermint Oil (Givauden Roure) | 1 (ex. 6) 2 (ex. 7) | 0.078 | 0.156 |
| Lecithin | 10.996 | 0.856 | 0.856 |
| Beeswax | 54.383 | 4.23 | 4.23 |
| Vitamin E | 15.2 | 1.18 | 1.18 |
| Total (Example 6) | 1284.371 | | |
| (Example 7) | 1284.371 | | |

The mixtures produced were pastes. The test subject reported that the fish oil was discernible (Example 10), but at a level much less than that for a comparative example in which the sorbitan mono oleate and polysorbate were omitted. The peppermint flavor was not noticeable. Doubling the Peppermint oil level (Example 11) improved the taste markedly and the peppermint flavor started to make the fish oil taste less prominent in the mouth.

EXAMPLE 12

| Material | mg/capsule equivalent | % |
| --- | --- | --- |
| Calcium Carbonate BP/EP | 677.112 | 53.84 |
| Cod Liver Oil | 500 | 39.75 |
| Sorbitan Mono-oleate BP | 34.96 | 2.78 |
| POLYSORBATE 80 BP (hydrophilic surfactant) | 17.48 | 1.39 |
| Peppermint Oil (Givauden Roure) | 2 | 0.16 |
| Lecithin | 10.996 | 0.875 |
| Beeswax | 54.383 | 4.32 |
| Vitamin E | 15.2 | 1.2 |
| Total | 1257.748 | |

The mixture produced was a paste. The test subject reported that the fish oil was barely discernible and, although not particularly pleasant, fish oil could not be identified as the cause.

EXAMPLE 13

| Material | mg/Capsule Equivalent | % |
| --- | --- | --- |
| Calcium Carbonate BP/EP | 677.112 | 50.53 |
| Cod Liver Oil | 500 | 37.31 |
| Sorbitan Mono-oleate BP | 53.52 | 3.99 |
| POLYSORBATE 80 BP (hydrophilic surfactant) | 26.76 | 2 |
| Peppermint Oil (Givauden Roure) | 2 | 0.149 |
| Lecithin | 10.996 | 0.82 |
| Beeswax | 54.383 | 4.06 |
| Vitamin E | 15.2 | 1.13 |
| Total | 1339.971 | |

The mixture produced was a paste. The test subject reported that the mixture had a chalky peppermint taste with no fish taste being discernible

What is claimed is:

1. A capsule for delivering an odoriferous oil and having reduced post-ingestion odor, said capsule containing an ingestible composition comprising:
    a digestible odoriferous oil selected from a fish oil or a mixture of fish oils;
    an edible odor-masking ingredient selected from the group consisting of parsley seed oil, lemon balm, lemon grass oil, fennel oil, peppermint oil, menthol, and combinations thereof; and
    an edible surfactant comprising a mixture of at least one hydrophilic surfactant and at least one lipophilic surfactant,
    wherein said digestible odoriferous oil is present in an amount ranging from about 30 to about 98% by weight of the ingestible composition,
    wherein said edible surfactant is present in an amount ranging from about 2 to about 20% by weight of the ingestible composition,
    wherein no water is added to the ingestible composition,
    wherein said ingestible composition upon ingestion forms an emulsion in the stomach,
    and
    wherein the weight ratio of said at least one hydrophilic surfactant to said at least one lipophilic surfactant is in the range of about 1:1.5 to about 1:2.5.

2. The capsule as claimed in claim 1, wherein the ingestible composition is in a continuous phase.

3. The capsule as claimed in claim 1, wherein the ingestible composition is a paste.

4. The capsule as claimed in claim 1, wherein said edible surfactant is present in an amount ranging from about 2 to about 10% by weight of the ingestible composition.

5. The capsule as claimed in claim 4, wherein said edible surfactant is present in an amount ranging from about 2 to about 7% by weight of the ingestible composition.

6. The capsule as claimed in claim 5, wherein said edible surfactant is present in an amount ranging from about 5 to about 7% by weight of the ingestible composition.

7. The capsule as claimed in claim 1, wherein said edible odor-masking ingredient includes at least one odor-masking oil.

8. The capsule as claimed in claim 1, wherein said edible odor-masking ingredient is present in an amount ranging from about 0.01 to about 5% based on the weight of said at least one digestible odoriferous oil.

9. The capsule as claimed in claim 1, wherein the at least one hydrophilic surfactant is selected from the group consisting of polyoxyethylene glycerides of $C_{10}$ to $C_{18}$ fatty acids, polyoxyethylene hydrogenated castor oils, and combinations thereof.

10. The capsule as claimed in claim 1, wherein the at least one lipophilic surfactant is selected from one or more glycerides of $C_5$ to $C_{10}$ fatty acids.

11. The capsule as claimed in claim 1, wherein the weight ratio of said at least one hydrophilic surfactant to said at least one lipophilic surfactant is in the range of about 1:1.7 to about 1:2.1.

12. The capsule as claimed in claim 1, wherein said digestible odoriferous oil is present in an amount ranging from about 75 to about 98% by weight of the ingestible composition.

13. The capsule as claimed in claim 1, wherein said digestible odoriferous oil is present in an amount ranging from about 85 to about 98% by weight of the ingestible composition.

14. The capsule as claimed in claim 1, wherein the fish oil comprises cod liver oil.

15. A capsule for delivering an odoriferous oil and having reduced post-ingestion odor, said capsule containing an ingestible composition comprising:

a digestible odoriferous oil selected from a fish oil or a mixture of fish oils;

an edible odor-masking ingredient selected from the group consisting of parsley seed oil, lemon balm, lemon grass oil, fennel oil, peppermint oil, menthol, and combinations thereof; and an edible surfactant comprising a mixture of a hydrophilic surfactant and a lipophilic surfactant, wherein said digestible odoriferous oil is present in an amount ranging from about 30 to about 98% by weight of the ingestible composition, wherein said edible surfactant is present in an amount ranging from about 2 to about 20% by weight of the ingestible composition, wherein no water is added to the ingestible composition, wherein said ingestible composition upon ingestion forms an emulsion in the stomach, and wherein the weight ratio of the hydrophilic surfactant to the lipophilic surfactant is about 1:2.

16. The capsule as claimed in claim 15, wherein the fish oil comprises cod liver oil.

* * * * *